(12) United States Patent
Webb

(10) Patent No.: US 11,364,110 B2
(45) Date of Patent: Jun. 21, 2022

(54) INTRAOCULAR IMPLANT WITH REMOVABLE OPTIC

(71) Applicant: AcuFocus, Inc., Irvine, CA (US)

(72) Inventor: R. Kyle Webb, Carlsbad, CA (US)

(73) Assignee: AcuFocus, Inc., Irvine, CA (US)

(*) Notice: Subject to any disclaimer, the term of this patent is extended or adjusted under 35 U.S.C. 154(b) by 0 days.

(21) Appl. No.: 17/053,052

(22) PCT Filed: May 7, 2019

(86) PCT No.: PCT/US2019/031189
§ 371 (c)(1),
(2) Date: Nov. 4, 2020

(87) PCT Pub. No.: WO2019/217471
PCT Pub. Date: Nov. 14, 2019

(65) Prior Publication Data
US 2021/0137674 A1 May 13, 2021

Related U.S. Application Data

(60) Provisional application No. 62/669,295, filed on May 9, 2018.

(51) Int. Cl.
*A61F 2/16* (2006.01)
(52) U.S. Cl.
CPC .......... *A61F 2/1624* (2013.01); *A61F 2/1613* (2013.01); *A61F 2/1648* (2013.01);
(Continued)

(58) Field of Classification Search
CPC .... A61F 2002/1696; A61F 2002/16902; A61F 2/1613; A61F 2/1648; A61F 2002/1681; A61F 2002/169; A61F 2250/0053
See application file for complete search history.

(56) References Cited

U.S. PATENT DOCUMENTS

| 2,350,421 A | 6/1944 | Schoder et al. |
| 2,470,927 A | 5/1949 | Hale, Jr. |

(Continued)

FOREIGN PATENT DOCUMENTS

| AU | 2004201751 | 5/2004 |
| CN | 1734305 A | 2/2006 |

(Continued)

OTHER PUBLICATIONS

Internet Archive Wayback Machine; Aniridia Implants; downloaded from https://web.archive.org/web/20110824062840/http://www.morcher.com/nc/produkte/aniridiaimplants.html (Archived Aug. 24, 2011; printed on Feb. 5, 2015).

(Continued)

*Primary Examiner* — Javier G Blanco
(74) *Attorney, Agent, or Firm* — Knobbe, Martens, Olson & Bear, LLP

(57) ABSTRACT

Intraocular implants and methods of forming intraocular implants are described herein. The intraocular implant can include a powered optic and a lens holder. The optic can be mechanically coupled to an inner periphery of the lens holder to form the intraocular implant. A portion of the lens holder can include a mask disposed about the optic to increase depth of focus in a human patient.

9 Claims, 8 Drawing Sheets

(52) U.S. Cl.
CPC .......... A61F 2002/1681 (2013.01); A61F 2002/1696 (2015.04); A61F 2002/16902 (2015.04)

(56) References Cited

U.S. PATENT DOCUMENTS

| | | |
|---|---|---|
| 3,034,403 A | 5/1962 | Neefe |
| 3,270,099 A | 8/1966 | Camp |
| 3,458,870 A | 8/1969 | Stone |
| 3,578,850 A | 5/1971 | Grant |
| 3,776,230 A | 12/1973 | Neefe |
| 3,794,414 A | 2/1974 | Wesley |
| 3,877,502 A | 4/1975 | Hunckler |
| 3,996,627 A | 12/1976 | Deeg et al. |
| 4,010,496 A | 3/1977 | Neefe |
| 4,104,338 A | 8/1978 | Guerrieri |
| 4,116,439 A | 9/1978 | Chavarria et al. |
| 4,210,391 A | 7/1980 | Cohen |
| 4,298,996 A | 11/1981 | Barnet |
| 4,340,283 A | 7/1982 | Cohen |
| 4,402,396 A | 9/1983 | Graham |
| 4,402,579 A | 9/1983 | Poler |
| 4,423,728 A | 1/1984 | Lieberman |
| 4,435,050 A | 3/1984 | Poler |
| 4,450,593 A | 5/1984 | Poler |
| 4,470,159 A | 9/1984 | Peyman |
| 4,505,855 A | 3/1985 | Bruns et al. |
| 4,512,039 A | 4/1985 | Lieberman |
| 4,563,565 A | 1/1986 | Kampfer et al. |
| 4,575,373 A | 3/1986 | Johnson |
| 4,596,578 A | 6/1986 | Kelman |
| 4,607,617 A | 8/1986 | Choyce |
| 4,624,669 A | 11/1986 | Grendahl |
| 4,639,105 A | 1/1987 | Neefe |
| 4,646,720 A | 3/1987 | Peyman et al. |
| 4,655,774 A | 4/1987 | Choyce |
| 4,665,913 A | 5/1987 | Esperance, Jr. |
| 4,669,466 A | 6/1987 | L'Esperance |
| 4,669,834 A | 6/1987 | Richter |
| 4,676,790 A | 6/1987 | Kern |
| 4,676,791 A | 6/1987 | LeMaster et al. |
| 4,678,422 A | 7/1987 | York |
| 4,701,038 A | 10/1987 | Neefe |
| 4,715,858 A | 12/1987 | Lindstrom |
| 4,744,647 A | 5/1988 | Meshel et al. |
| 4,767,647 A | 8/1988 | Bree |
| 4,795,462 A | 1/1989 | Grendahl |
| 4,798,608 A | 1/1989 | Grendahl |
| 4,799,784 A | 1/1989 | Safir |
| 4,799,931 A | 1/1989 | Lindstrom |
| 4,807,623 A | 2/1989 | Lieberman |
| 4,813,955 A | 3/1989 | Achatz et al. |
| 4,815,690 A | 3/1989 | Shepherd |
| 4,817,789 A | 4/1989 | Paul |
| 4,830,855 A | 5/1989 | Stewart |
| 4,842,599 A | 6/1989 | Bronstein |
| 4,842,782 A | 6/1989 | Portney |
| 4,851,003 A | 7/1989 | Lindstrom |
| 4,863,466 A | 9/1989 | Schlegel |
| 4,881,860 A | 11/1989 | Kanazawa |
| 4,903,695 A | 2/1990 | Warner et al. |
| 4,907,586 A | 3/1990 | Bille et al. |
| 4,928,815 A | 5/1990 | Paul |
| 4,955,904 A | 9/1990 | Atebara et al. |
| 4,976,732 A | 12/1990 | Vorosmarthy |
| 4,994,080 A | 2/1991 | Shepard |
| 5,013,319 A | 5/1991 | Davis |
| 5,030,230 A | 7/1991 | White |
| 5,034,166 A | 7/1991 | Rawlings et al. |
| 5,041,133 A | 8/1991 | Sayano et al. |
| 5,055,602 A | 10/1991 | Melpolder |
| 5,087,015 A | 2/1992 | Galley |
| 5,090,955 A | 2/1992 | Simon |
| 5,092,880 A | 3/1992 | Ohmi |
| 5,094,521 A | 3/1992 | Jolson et al. |
| 5,098,443 A | 3/1992 | Parel et al. |
| 5,108,427 A | 4/1992 | Majercik et al. |
| 5,112,328 A | 5/1992 | Taboada et al. |
| 5,120,120 A | 6/1992 | Cohen |
| 5,120,121 A | 6/1992 | Rawlings et al. |
| 5,137,441 A | 8/1992 | Fogarty |
| 5,147,395 A | 9/1992 | Willis |
| 5,171,318 A | 12/1992 | Gibson et al. |
| 5,185,107 A | 2/1993 | Blake |
| 5,188,494 A | 2/1993 | Hatin |
| 5,192,316 A | 3/1993 | Ting |
| 5,196,026 A | 3/1993 | Barrett et al. |
| 5,213,749 A | 5/1993 | Huss et al. |
| 5,260,727 A | 11/1993 | Oksman et al. |
| 5,266,241 A | 11/1993 | Parekh |
| 5,269,795 A | 12/1993 | Arnott |
| 5,269,812 A | 12/1993 | White |
| 5,274,404 A | 12/1993 | Michael |
| 5,288,436 A | 2/1994 | Liu et al. |
| 5,290,892 A | 3/1994 | Namdaran et al. |
| 5,292,514 A | 3/1994 | Capecchi et al. |
| 5,300,116 A | 4/1994 | Chirila et al. |
| 5,312,330 A | 5/1994 | Klopotek |
| 5,314,439 A | 5/1994 | Sugita |
| 5,314,961 A | 5/1994 | Anton et al. |
| 5,332,802 A | 7/1994 | Kelman et al. |
| 5,336,261 A | 8/1994 | Barrett et al. |
| 5,354,331 A | 10/1994 | Schachar et al. |
| 5,358,520 A | 10/1994 | Patel |
| 5,372,580 A | 12/1994 | Simon et al. |
| 5,391,201 A | 2/1995 | Barrett et al. |
| 5,441,511 A | 8/1995 | Hanna |
| 5,474,548 A | 12/1995 | Knopp et al. |
| 5,507,740 A | 4/1996 | O'Donnell, Jr. |
| 5,507,806 A | 4/1996 | Blake |
| 5,547,468 A | 4/1996 | Simon et al. |
| D375,245 S | 11/1996 | Irving |
| 5,578,080 A | 11/1996 | McDonald |
| 5,603,774 A | 2/1997 | LeBoeuf et al. |
| 5,607,437 A | 3/1997 | Simon et al. |
| 5,624,456 A | 4/1997 | Hellenkamp |
| 5,627,613 A | 5/1997 | Kaneko |
| 5,628,794 A | 5/1997 | Lindstrom |
| 5,628,795 A | 5/1997 | Langerman |
| 5,647,865 A | 7/1997 | Swinger |
| 5,652,638 A | 7/1997 | Roffman et al. |
| 5,653,752 A | 8/1997 | Silvestrini et al. |
| 5,662,706 A | 9/1997 | Legerton et al. |
| 5,674,284 A | 10/1997 | Chang et al. |
| 5,693,268 A | 12/1997 | Widman et al. |
| 5,697,923 A | 12/1997 | Poler |
| 5,702,440 A | 12/1997 | Portney |
| 5,708,049 A | 1/1998 | Katagiri et al. |
| 5,713,957 A | 2/1998 | Steele et al. |
| 5,722,971 A | 3/1998 | Peyman |
| 5,725,575 A | 3/1998 | O'Donnell, Jr. |
| 5,728,156 A | 3/1998 | Gupta et al. |
| 5,746,558 A | 5/1998 | Nygren et al. |
| 5,752,967 A | 5/1998 | Kritzinger et al. |
| 5,757,458 A | 5/1998 | Miller et al. |
| 5,769,889 A | 6/1998 | Kelman |
| 5,774,202 A | 6/1998 | Abraham et al. |
| 5,786,883 A | 7/1998 | Miller et al. |
| 5,824,086 A | 10/1998 | Silvestrini |
| 5,837,156 A | 11/1998 | Cumming |
| 5,843,105 A | 12/1998 | Mathis et al. |
| 5,864,128 A | 1/1999 | Plesko |
| 5,870,167 A | 2/1999 | Knopp et al. |
| 5,876,442 A | 3/1999 | Lipshitz et al. |
| 5,895,610 A | 4/1999 | Chang et al. |
| 5,905,561 A | 5/1999 | Lee et al. |
| 5,910,537 A | 6/1999 | Feingold et al. |
| 5,913,898 A | 6/1999 | Feingold et al. |
| 5,919,185 A | 7/1999 | Peyman |
| 5,925,294 A | 7/1999 | Shibuya |
| 5,964,748 A | 10/1999 | Peyman |
| 5,964,776 A | 10/1999 | Peyman |
| 5,965,330 A | 10/1999 | Evans et al. |
| 5,980,040 A | 11/1999 | Xu et al. |

(56) References Cited

U.S. PATENT DOCUMENTS

| | | | |
|---|---|---|---|
| 6,007,579 A * | 12/1999 | Lipshitz | A61F 2/1651 623/6.11 |
| 6,017,121 A | 1/2000 | Chateau et al. | |
| 6,063,073 A | 5/2000 | Peyman | |
| 6,090,141 A | 7/2000 | Lindstrom | |
| 6,102,946 A | 8/2000 | Nigam | |
| 6,106,553 A | 8/2000 | Feingold et al. | |
| 6,110,166 A | 8/2000 | Juhasz et al. | |
| 6,138,307 A | 10/2000 | McDonald | |
| 6,152,959 A | 11/2000 | Portney | |
| 6,164,777 A | 12/2000 | Li et al. | |
| 6,171,336 B1 | 1/2001 | Sawusch | |
| 6,178,593 B1 | 1/2001 | Carlson | |
| 6,197,019 B1 | 3/2001 | Peyman | |
| 6,201,036 B1 | 3/2001 | Fedorov et al. | |
| 6,203,538 B1 | 3/2001 | Peyman | |
| 6,210,401 B1 | 4/2001 | Lai | |
| 6,217,571 B1 | 4/2001 | Peyman | |
| 6,217,596 B1 | 4/2001 | Farah | |
| 6,221,067 B1 | 4/2001 | Peyman | |
| 6,228,113 B1 | 5/2001 | Kaufman | |
| 6,228,114 B1 | 5/2001 | Lee | |
| 6,228,115 B1 | 5/2001 | Hoffmann et al. | |
| 6,264,648 B1 | 7/2001 | Peyman | |
| 6,277,146 B1 * | 8/2001 | Peyman | A61F 2/1613 623/6.34 |
| 6,280,470 B1 | 8/2001 | Peyman | |
| 6,280,471 B1 | 8/2001 | Peyman et al. | |
| 6,302,877 B1 | 10/2001 | Ruiz | |
| 6,304,390 B1 | 10/2001 | Takanashi | |
| 6,308,590 B1 | 10/2001 | Berto | |
| 6,335,190 B1 | 1/2002 | Zhou et al. | |
| 6,361,560 B1 | 3/2002 | Nigam | |
| 6,376,153 B2 | 4/2002 | Uchikawa et al. | |
| 6,387,379 B1 | 5/2002 | Goldberg et al. | |
| 6,391,230 B1 | 5/2002 | Sarbadhikari | |
| 6,416,179 B1 | 7/2002 | Lieberman et al. | |
| 6,423,093 B1 | 7/2002 | Hicks et al. | |
| 6,432,246 B1 | 8/2002 | Blake | |
| 6,436,092 B1 | 8/2002 | Peyman | |
| 6,458,141 B1 | 10/2002 | Peyman | |
| 6,461,384 B1 | 10/2002 | Hoffmann et al. | |
| 6,469,844 B1 | 10/2002 | Iwase et al. | |
| 6,480,346 B2 | 11/2002 | Funakoshi | |
| 6,491,637 B2 | 12/2002 | Foster et al. | |
| 6,497,700 B1 | 12/2002 | LaHaye | |
| 6,515,006 B2 | 2/2003 | Horn | |
| 6,533,416 B1 | 3/2003 | Fermigier et al. | |
| 6,551,307 B2 | 4/2003 | Peyman | |
| 6,554,424 B1 | 4/2003 | Miller et al. | |
| 6,554,860 B2 | 4/2003 | Hoffmann et al. | |
| 6,555,103 B2 | 4/2003 | Leukel et al. | |
| 6,575,573 B2 | 6/2003 | Lai et al. | |
| 6,581,993 B2 | 6/2003 | Nigam | |
| 6,588,902 B2 | 7/2003 | Isogai | |
| 6,589,280 B1 | 7/2003 | Koziol | |
| 6,607,527 B1 | 8/2003 | Ruiz et al. | |
| 6,613,088 B1 | 9/2003 | Babizhayev | |
| 6,638,304 B2 | 10/2003 | Azar | |
| 6,649,722 B2 | 11/2003 | Rosenzweig et al. | |
| 6,655,804 B2 | 12/2003 | Streibig | |
| 6,692,126 B1 | 2/2004 | Xie et al. | |
| 6,702,807 B2 | 3/2004 | Peyman | |
| 6,726,322 B2 | 4/2004 | Andino et al. | |
| 6,740,116 B2 | 5/2004 | Morcher | |
| 6,755,858 B1 | 6/2004 | White | |
| 6,786,926 B2 | 9/2004 | Peyman | |
| 6,811,256 B1 | 11/2004 | Becherer et al. | |
| 6,855,163 B2 | 2/2005 | Peyman | |
| 6,874,886 B2 | 4/2005 | Miller et al. | |
| 6,899,424 B2 | 5/2005 | Miller et al. | |
| 6,949,093 B1 | 9/2005 | Peyman | |
| 6,951,556 B2 | 10/2005 | Epstein | |
| 6,966,648 B2 | 11/2005 | Miller et al. | |
| 6,989,008 B2 | 1/2006 | Peyman | |
| 6,997,428 B1 | 2/2006 | Andino et al. | |
| 7,001,374 B2 | 2/2006 | Peyman | |
| 7,008,447 B2 | 3/2006 | Koziol | |
| 7,025,455 B2 | 4/2006 | Roffman | |
| 7,061,693 B2 | 6/2006 | Zalevsky | |
| 7,099,057 B2 | 8/2006 | Parker et al. | |
| 7,276,080 B2 | 10/2007 | Murakami et al. | |
| 7,287,852 B2 | 10/2007 | Fiala | |
| 7,364,674 B1 | 4/2008 | Hoover | |
| 7,399,811 B2 | 7/2008 | Mentak et al. | |
| 7,404,637 B2 | 7/2008 | Miller et al. | |
| 7,404,638 B2 | 7/2008 | Miller et al. | |
| 7,446,157 B2 | 11/2008 | Mentak et al. | |
| 7,455,404 B2 | 11/2008 | Bandhauer et al. | |
| 7,455,691 B2 | 11/2008 | Feingold et al. | |
| 7,462,193 B2 | 12/2008 | Nagamoto | |
| 7,477,452 B2 | 1/2009 | Tsuruma | |
| 7,491,350 B2 | 1/2009 | Silvestrini | |
| 7,497,866 B2 | 3/2009 | Perez | |
| 7,628,810 B2 | 12/2009 | Christie et al. | |
| 7,632,431 B2 | 12/2009 | Ghazizadeh et al. | |
| 7,641,337 B2 | 1/2010 | Altmann | |
| 7,645,299 B2 | 1/2010 | Koziol | |
| 7,745,555 B2 | 6/2010 | Mentak et al. | |
| 7,780,290 B2 | 8/2010 | Zhao | |
| 7,842,367 B2 | 11/2010 | Mentak | |
| 7,976,577 B2 | 7/2011 | Silvestrini | |
| D645,337 S | 9/2011 | Hsu et al. | |
| 8,043,371 B2 | 10/2011 | Paul et al. | |
| 8,048,972 B2 | 11/2011 | Mentak et al. | |
| 8,079,706 B2 | 12/2011 | Silvestrini et al. | |
| D656,526 S | 3/2012 | Christie et al. | |
| 8,157,374 B2 | 4/2012 | Bandhauer et al. | |
| 8,241,354 B2 | 8/2012 | Hong et al. | |
| 8,287,592 B2 | 10/2012 | Silvestrini | |
| 8,343,215 B2 | 1/2013 | Miller et al. | |
| D681,086 S | 4/2013 | Christie et al. | |
| 8,420,753 B2 | 4/2013 | Mentak et al. | |
| 8,439,498 B2 | 5/2013 | Zhao et al. | |
| 8,460,374 B2 | 6/2013 | Christie et al. | |
| 8,562,131 B2 | 10/2013 | Zhao | |
| 8,604,098 B2 | 12/2013 | Boydston et al. | |
| 8,740,978 B2 | 6/2014 | Weeber et al. | |
| 8,747,466 B2 | 6/2014 | Weeber et al. | |
| 8,752,958 B2 | 6/2014 | Miller et al. | |
| 8,633,292 B2 | 7/2014 | Hu et al. | |
| 8,814,934 B2 * | 8/2014 | Geraghty | A61F 2/1613 623/6.37 |
| 8,858,624 B2 | 10/2014 | Christie et al. | |
| 8,864,824 B2 | 10/2014 | Silvestrini et al. | |
| 8,955,968 B2 | 2/2015 | Zalevsky et al. | |
| 9,005,281 B2 * | 4/2015 | Christie | A61F 2/1659 623/6.17 |
| 9,138,142 B2 | 9/2015 | Christie et al. | |
| 9,204,962 B2 | 12/2015 | Silvestrini | |
| 9,358,103 B1 | 6/2016 | Wortz et al. | |
| 9,427,311 B2 | 8/2016 | Christie et al. | |
| 9,427,922 B2 | 8/2016 | Reboul et al. | |
| 9,492,272 B2 | 11/2016 | Christie et al. | |
| 9,545,303 B2 | 1/2017 | Vilupuru et al. | |
| 9,573,328 B2 | 2/2017 | Reboul et al. | |
| 9,603,704 B2 | 3/2017 | Silvestrini | |
| 9,744,077 B2 | 8/2017 | Zicker et al. | |
| 9,757,227 B2 | 9/2017 | Kushlin et al. | |
| 9,844,919 B2 | 12/2017 | Reboul et al. | |
| 9,848,979 B2 | 12/2017 | Vilupuru et al. | |
| 9,943,403 B2 | 4/2018 | Webb et al. | |
| 9,987,127 B2 | 6/2018 | Bogaert et al. | |
| 10,004,593 B2 | 6/2018 | Webb et al. | |
| 10,183,453 B2 | 1/2019 | Reboul et al. | |
| 10,342,656 B2 | 7/2019 | Vilupuru et al. | |
| 10,350,058 B2 | 7/2019 | Silvestrini | |
| 10,426,600 B2 | 10/2019 | Coleman et al. | |
| 10,449,036 B2 | 10/2019 | Christie et al. | |
| 10,548,717 B2 | 2/2020 | Webb et al. | |
| 10,583,619 B2 | 3/2020 | Reboul et al. | |
| 10,687,935 B2 | 6/2020 | Webb et al. | |
| 10,765,508 B2 | 9/2020 | Vilupuru et al. | |
| 10,869,752 B2 | 12/2020 | Christie et al. | |

(56) References Cited

U.S. PATENT DOCUMENTS

| | | |
|---|---|---|
| 10,932,902 B2 | 3/2021 | Reedy et al. |
| 10,939,995 B2 | 3/2021 | Silvestrini |
| 2001/0027314 A1 | 10/2001 | Peyman |
| 2001/0034516 A1 | 10/2001 | Peyman |
| 2001/0050750 A1 | 12/2001 | Breger |
| 2002/0010510 A1 | 1/2002 | Silverstrini |
| 2002/0082288 A1 | 6/2002 | Horn |
| 2002/0120329 A1 | 8/2002 | Lang et al. |
| 2002/0128710 A1* | 9/2002 | Eggleston ............ A61F 2/1613 623/6.22 |
| 2002/0167640 A1 | 11/2002 | Francis et al. |
| 2002/0196409 A1 | 12/2002 | Jani |
| 2003/0014042 A1 | 1/2003 | Juhasz et al. |
| 2003/0060880 A1 | 3/2003 | Feingold |
| 2003/0105521 A1 | 6/2003 | Perez |
| 2003/0135272 A1 | 7/2003 | Brady et al. |
| 2003/0149480 A1 | 8/2003 | Shadduck |
| 2003/0204258 A1 | 10/2003 | Graham et al. |
| 2003/0216763 A1 | 11/2003 | Patel |
| 2004/0019379 A1 | 1/2004 | Glick et al. |
| 2004/0056371 A1 | 3/2004 | Liao et al. |
| 2004/0068317 A1 | 4/2004 | Knight |
| 2004/0106929 A1 | 6/2004 | Masket |
| 2004/0140578 A1 | 7/2004 | Kelly et al. |
| 2005/0027355 A1 | 2/2005 | Murakami et al. |
| 2005/0046794 A1 | 3/2005 | Silvestrini et al. |
| 2005/0056954 A1 | 3/2005 | Devlin |
| 2005/0090895 A1 | 4/2005 | Peyman |
| 2005/0124983 A1 | 6/2005 | Frey et al. |
| 2005/0134793 A1 | 6/2005 | Roffman |
| 2005/0137703 A1 | 6/2005 | Chen |
| 2005/0143751 A1 | 6/2005 | Makker et al. |
| 2005/0143813 A1 | 6/2005 | Hovey et al. |
| 2005/0182488 A1 | 8/2005 | Peyman |
| 2005/0182489 A1 | 8/2005 | Peyman |
| 2005/0187621 A1 | 8/2005 | Brady |
| 2005/0288784 A1 | 12/2005 | Peyman |
| 2006/0064077 A1 | 3/2006 | Peyman |
| 2006/0079959 A1 | 4/2006 | Christie et al. |
| 2006/0113054 A1 | 6/2006 | Silvestrini |
| 2006/0135477 A1 | 6/2006 | Haitjema et al. |
| 2006/0184243 A1 | 8/2006 | Yilmaz |
| 2006/0232665 A1 | 10/2006 | Schowengerdt et al. |
| 2006/0235428 A1 | 10/2006 | Silvestrini |
| 2006/0235514 A1 | 10/2006 | Silvestrini |
| 2006/0241751 A1 | 10/2006 | Marmo et al. |
| 2006/0247659 A1 | 11/2006 | Moeller et al. |
| 2006/0265058 A1 | 11/2006 | Silvestrini |
| 2006/0268226 A1 | 11/2006 | Christie et al. |
| 2006/0268227 A1 | 11/2006 | Christie et al. |
| 2006/0268228 A1 | 11/2006 | Christie et al. |
| 2006/0268229 A1 | 11/2006 | Silvestrini et al. |
| 2006/0270946 A1 | 11/2006 | Silvestrini et al. |
| 2006/0271026 A1 | 11/2006 | Silvestrini et al. |
| 2006/0271178 A1 | 11/2006 | Christie et al. |
| 2006/0271179 A1 | 11/2006 | Christie et al. |
| 2006/0271180 A1 | 11/2006 | Christie et al. |
| 2006/0271181 A1 | 11/2006 | Christie et al. |
| 2006/0271182 A1 | 11/2006 | Christie et al. |
| 2006/0271183 A1 | 11/2006 | Christie et al. |
| 2006/0271184 A1 | 11/2006 | Silvestrini |
| 2006/0271185 A1 | 11/2006 | Silvestrini |
| 2006/0274264 A1 | 12/2006 | Christie et al. |
| 2006/0274265 A1 | 12/2006 | Christie et al. |
| 2007/0021832 A1 | 1/2007 | Nordan |
| 2007/0032866 A1 | 2/2007 | Portney |
| 2007/0091472 A1 | 4/2007 | Alkemper et al. |
| 2007/0092592 A1 | 4/2007 | Chiang |
| 2007/0129797 A1 | 6/2007 | Lang et al. |
| 2007/0225691 A1 | 9/2007 | Silvestrini et al. |
| 2008/0033546 A1 | 2/2008 | Liang |
| 2008/0077238 A1 | 3/2008 | Deacon et al. |
| 2008/0100921 A1 | 5/2008 | Nishikawa |
| 2008/0151183 A1 | 6/2008 | Altmann |
| 2008/0208335 A1 | 8/2008 | Blum et al. |
| 2008/0212030 A1 | 9/2008 | Bentley et al. |
| 2008/0220214 A1 | 9/2008 | Uozu et al. |
| 2008/0221674 A1 | 9/2008 | Blum et al. |
| 2008/0221676 A1* | 9/2008 | Coleman ............... A61F 2/1643 623/6.23 |
| 2008/0255663 A1 | 10/2008 | Akpek et al. |
| 2008/0269884 A1 | 10/2008 | Vannoy |
| 2008/0288066 A1 | 11/2008 | Cumming |
| 2008/0306587 A1 | 12/2008 | Your |
| 2009/0012505 A1 | 1/2009 | Chernyak |
| 2009/0021692 A1 | 1/2009 | Miller et al. |
| 2009/0287306 A1 | 1/2009 | Smith et al. |
| 2009/0036880 A1 | 2/2009 | Bischoff et al. |
| 2009/0048608 A1 | 2/2009 | Boukhny et al. |
| 2009/0059168 A1 | 3/2009 | Miller et al. |
| 2009/0069817 A1 | 3/2009 | Peyman |
| 2009/0164008 A1 | 6/2009 | Hong et al. |
| 2009/0171458 A1 | 7/2009 | Kellan et al. |
| 2009/0187242 A1 | 7/2009 | Weeber et al. |
| 2009/0204207 A1 | 8/2009 | Blum et al. |
| 2009/0213326 A1 | 8/2009 | Zhao |
| 2009/0222086 A1 | 9/2009 | Lui et al. |
| 2009/0234448 A1 | 9/2009 | Weeber et al. |
| 2009/0279048 A1 | 11/2009 | Hong et al. |
| 2009/0306773 A1 | 12/2009 | Silvestrini et al. |
| 2009/0323020 A1 | 12/2009 | Zhao et al. |
| 2010/0016961 A1 | 1/2010 | Hong et al. |
| 2010/0016965 A1 | 1/2010 | Hong et al. |
| 2010/0082017 A1 | 4/2010 | Zickler et al. |
| 2010/0082100 A1 | 4/2010 | Mikawa |
| 2010/0127412 A1 | 5/2010 | Lake |
| 2010/0149618 A1 | 6/2010 | Sprague |
| 2010/0208199 A1 | 8/2010 | Levis et al. |
| 2010/0225014 A1 | 9/2010 | Bille |
| 2010/0312336 A1 | 12/2010 | Hong et al. |
| 2011/0029074 A1* | 2/2011 | Reisin .................... A61F 9/007 606/107 |
| 2011/0037184 A1 | 2/2011 | Shoji et al. |
| 2011/0051080 A1 | 3/2011 | Bandhauer et al. |
| 2011/0125261 A1 | 5/2011 | Portney |
| 2011/0140333 A1 | 6/2011 | Schaper et al. |
| 2011/0166652 A1 | 7/2011 | Bogaert et al. |
| 2011/0172675 A1 | 7/2011 | Danta et al. |
| 2011/0245919 A1 | 10/2011 | Pettit |
| 2011/0251685 A1 | 10/2011 | Chu |
| 2011/0292340 A1 | 12/2011 | Shimizu et al. |
| 2012/0203239 A1 | 8/2012 | Vukich et al. |
| 2012/0245683 A1 | 9/2012 | Christie et al. |
| 2012/0309761 A1 | 12/2012 | Chow et al. |
| 2012/0310338 A1 | 12/2012 | Christie et al. |
| 2013/0053953 A1 | 2/2013 | Silvestrini |
| 2013/0131795 A1 | 5/2013 | Miller et al. |
| 2013/0147072 A1 | 6/2013 | Bothe et al. |
| 2013/0190868 A1* | 7/2013 | Kahook ................ A61F 2/1613 623/6.38 |
| 2013/0238091 A1 | 9/2013 | Danta et al. |
| 2013/0289543 A1 | 10/2013 | Mordaunt |
| 2013/0324983 A1 | 12/2013 | Liang |
| 2014/0121767 A1 | 5/2014 | Simpson |
| 2014/0131905 A1 | 5/2014 | Webb |
| 2014/0200666 A1 | 7/2014 | Phillips |
| 2014/0277437 A1 | 9/2014 | Currie |
| 2014/0336625 A1 | 11/2014 | Fernandez |
| 2014/0343541 A1 | 11/2014 | Scott et al. |
| 2014/0379078 A1 | 12/2014 | Trindade |
| 2015/0025627 A1 | 1/2015 | Christie et al. |
| 2015/0046094 A1 | 2/2015 | Chaudhary et al. |
| 2015/0073549 A1 | 3/2015 | Webb et al. |
| 2015/0177422 A1 | 6/2015 | Liu et al. |
| 2015/0183173 A1 | 7/2015 | Linhardt et al. |
| 2015/0250583 A1 | 9/2015 | Rosen et al. |
| 2015/0366658 A1 | 12/2015 | Christie et al. |
| 2016/0100938 A1 | 4/2016 | Bogaert et al. |
| 2016/0297107 A1 | 10/2016 | Shim et al. |
| 2017/0049560 A1 | 2/2017 | Cherne |
| 2017/0143477 A1 | 5/2017 | Christie et al. |
| 2017/0156850 A1 | 6/2017 | Silvestrini et al. |
| 2018/0296322 A1 | 10/2018 | Webb et al. |
| 2018/0338826 A1 | 11/2018 | Link et al. |

(56) References Cited

U.S. PATENT DOCUMENTS

| | | | |
|---|---|---|---|
| 2019/0076241 A1 | 3/2019 | Alarcon Heredia et al. |
| 2019/0193350 A1 | 6/2019 | Gu et al. |
| 2019/0269499 A1 | 9/2019 | Ellis |
| 2020/0000576 A1 | 1/2020 | Christie et al. |
| 2020/0008932 A1 | 1/2020 | Silvestrini |
| 2020/0179105 A1 | 6/2020 | Waterhouse et al. |
| 2020/0253721 A1 | 8/2020 | Cuevas et al. |
| 2020/0337831 A1 | 10/2020 | Webb et al. |
| 2020/0337834 A1 | 10/2020 | Webb et al. |
| 2021/0015604 A1 | 1/2021 | Ma |
| 2021/0154002 A1 | 5/2021 | Christie et al. |

FOREIGN PATENT DOCUMENTS

| | | |
|---|---|---|
| CN | 1875895 | 12/2006 |
| CN | 100368846 C | 2/2008 |
| CN | 101322663 | 12/2008 |
| CN | 102448404 | 5/2012 |
| CN | 101341426 B | 7/2012 |
| CN | 203647535 U | 6/2014 |
| DE | 2727410 A1 | 12/1978 |
| DE | 4134320 | 4/1992 |
| EP | 0165652 | 12/1985 |
| EP | 0443094 | 8/1991 |
| EP | 1173790 | 1/2002 |
| EP | 1674049 | 6/2006 |
| EP | 1548489 B1 | 8/2006 |
| EP | 2111822 | 10/2009 |
| EP | 2319457 | 5/2011 |
| EP | 2243052 B1 | 9/2011 |
| EP | 2365379 | 9/2011 |
| EP | 2455799 | 5/2012 |
| EP | 2823789 | 1/2015 |
| EP | 2364457 B1 | 8/2015 |
| EP | 2993514 A1 | 3/2016 |
| EP | 2349150 B1 | 7/2016 |
| FR | 2620687 | 3/1989 |
| FR | 2649605 | 1/1991 |
| GB | 1276003 | 6/1972 |
| GB | 2507465 | 5/2014 |
| JP | 62-167343 | 7/1987 |
| JP | 64-002644 | 1/1989 |
| JP | H01-195852 | 8/1989 |
| JP | H02-7954 | 1/1990 |
| JP | 04-158859 | 6/1992 |
| JP | 06-509731 | 3/1993 |
| JP | H05-65340 | 9/1993 |
| JP | 06-502782 | 3/1994 |
| JP | H07-067896 | 3/1995 |
| JP | 07-265340 | 10/1995 |
| JP | 08-103457 A | 4/1996 |
| JP | H09-502542 | 3/1997 |
| JP | 11-503657 | 8/1997 |
| JP | 07-178125 | 7/1998 |
| JP | 2000-047145 | 2/2000 |
| JP | 2002-537895 | 11/2002 |
| JP | 2003-502109 | 1/2003 |
| JP | 2004-510199 | 4/2004 |
| JP | 2004-538034 | 12/2004 |
| JP | 2005-533576 | 11/2005 |
| JP | 2007-516794 | 6/2007 |
| JP | 2007-523720 | 8/2007 |
| JP | 2008-506710 | 3/2008 |
| JP | S59-54527 | 5/2008 |
| JP | 2013-501598 | 1/2013 |
| JP | 2015-077412 | 4/2015 |
| KR | 10-0335722 | 5/2002 |
| KR | 10-2012-0093837 | 8/2012 |
| RU | 2138837 | 9/1999 |
| RU | 110978 U | 3/2011 |
| RU | 2456968 | 7/2012 |
| RU | 2457812 | 8/2012 |
| RU | 2459598 | 8/2012 |
| RU | 2493801 | 9/2013 |
| RU | 134049 | 11/2013 |
| RU | 134784 | 11/2013 |
| RU | 2500368 | 12/2013 |
| RU | 2511081 | 4/2014 |
| RU | 2517488 | 5/2014 |
| SU | 1380743 A1 | 3/1988 |
| TW | 201103518 | 2/2011 |
| WO | WO 87/05797 | 10/1987 |
| WO | WO 95/03747 | 2/1995 |
| WO | WO 95/08135 | 3/1995 |
| WO | WO 96/35397 | 11/1996 |
| WO | WO 98/48715 | 11/1998 |
| WO | WO 00/025704 | 5/2000 |
| WO | WO 00/038594 | 7/2000 |
| WO | WO 00/51682 | 9/2000 |
| WO | WO 00/52516 | 9/2000 |
| WO | WO 00/70388 | 11/2000 |
| WO | WO 2001/010641 | 2/2001 |
| WO | WO 01/15779 | 3/2001 |
| WO | WO 01/17460 | 3/2001 |
| WO | WO 01/19364 | 3/2001 |
| WO | WO 01/082815 | 11/2001 |
| WO | WO 02/076320 | 10/2002 |
| WO | WO 02/102241 | 12/2002 |
| WO | WO 03/020177 | 3/2003 |
| WO | WO 03/022168 | 3/2003 |
| WO | WO 03/061518 | 7/2003 |
| WO | WO 2004/014969 | 2/2004 |
| WO | WO 2004/034917 | 4/2004 |
| WO | WO 2004/105588 | 12/2004 |
| WO | WO 2004/113959 | 12/2004 |
| WO | WO 2005/023154 | 3/2005 |
| WO | WO 2005/082265 | 9/2005 |
| WO | WO 2006/014738 | 2/2006 |
| WO | WO 2006/020638 | 2/2006 |
| WO | WO 2006/047534 | 5/2006 |
| WO | WO 2006/060380 | 6/2006 |
| WO | WO 2006/069012 | 6/2006 |
| WO | WO 2006/113377 | 10/2006 |
| WO | WO 2006/113411 | 10/2006 |
| WO | WO 2006/113563 | 10/2006 |
| WO | WO 2006/113564 | 10/2006 |
| WO | WO 2007/057734 | 10/2007 |
| WO | WO 2007/133384 | 11/2007 |
| WO | WO 2007/142981 | 12/2007 |
| WO | WO 2008/036671 | 3/2008 |
| WO | WO 2008/102096 | 8/2008 |
| WO | WO 2009/050511 | 4/2009 |
| WO | WO 2009/122409 | 10/2009 |
| WO | WO 2009/140080 | 11/2009 |
| WO | WO 2009/149060 | 12/2009 |
| WO | WO 2010/002215 | 1/2010 |
| WO | WO 2010/059214 | 5/2010 |
| WO | WO 2010/118469 | 10/2010 |
| WO | WO 2011/020074 | 2/2011 |
| WO | WO 2011/020078 | 2/2011 |
| WO | WO 2011/047076 | 4/2011 |
| WO | WO 2011/069059 | 6/2011 |
| WO | WO 2011/088107 | 7/2011 |
| WO | WO 2012/170066 | 12/2012 |
| WO | WO 2011/030509 | 2/2013 |
| WO | WO 2013/019871 | 2/2013 |
| WO | WO 2013/082545 | 6/2013 |
| WO | WO 2013/101793 | 7/2013 |
| WO | WO 2013/112589 | 8/2013 |
| WO | WO 2013/123265 | 8/2013 |
| WO | WO 2014/054946 | 4/2014 |
| WO | WO 2014/074610 | 5/2014 |
| WO | WO 2014/158653 | 10/2014 |
| WO | WO 2014/164056 | 10/2014 |
| WO | WO 2014/195059 | 12/2014 |
| WO | WO 2015/021323 | 2/2015 |
| WO | WO 2015/069927 | 5/2015 |
| WO | WO 2015/073718 | 5/2015 |
| WO | WO 2015/078271 | 6/2015 |
| WO | WO 2015/086611 | 6/2015 |
| WO | WO 2016/081493 | 5/2016 |
| WO | WO 2015/108156 | 3/2017 |

(56) References Cited

FOREIGN PATENT DOCUMENTS

| WO | WO 2017/062316 | 4/2017 |
| WO | WO 2017/091520 | 6/2017 |
| WO | WO 2019/010178 | 1/2019 |

OTHER PUBLICATIONS

Guyton A.C., Textbook of Medical Physiology, 7th Edition, W.B. Saunders Company, Jan. 1986: Chapter 58, in 13 pages.

Lu Xuequan, et al. "Radiation preparation and thermo-response swelling of interpenetrating polymer network hydrogel composed of PNIPAAm and PMMA", Radiation Physics and Chemistry, vol. 57, Mar. 2000, pp. 477-480, XP002473596.

Patel, C.K., et al. "Imaging the macula through a black occlusive intraocular lens". Arch. Ophthalmol. Oct. 2010; 128(10):1374-1376.

Reper-NN LTD, Instruction for Use. MOIL-Iris Iris-intaocular polymer elastic lenses, dated Aug. 2017, in 8 pages.

Yusuf, et al., "Inability to perform posterior segment monitoring by scanning laser ophthalmoscopy or optical coherence tomography with some occlusive intraocular lenses in clinical use", J. Cataract Refract. Surg., Mar. 2012, 38: 513-518.

Yusuf, et al., "Occlusive IOLs for Intractable Diplopia Demonstrate a Novel Near-Infrared Window of Transmission for SLO/OCT Imaging and Clinical Assessment". Investigative Ophthalmology & Visual Science, May 2011, 52(6): 3737-3743.

International Search Report and Written Opinion of PCT/US2019/031189, dated Aug. 9, 2019, in 11 pages.

\* cited by examiner

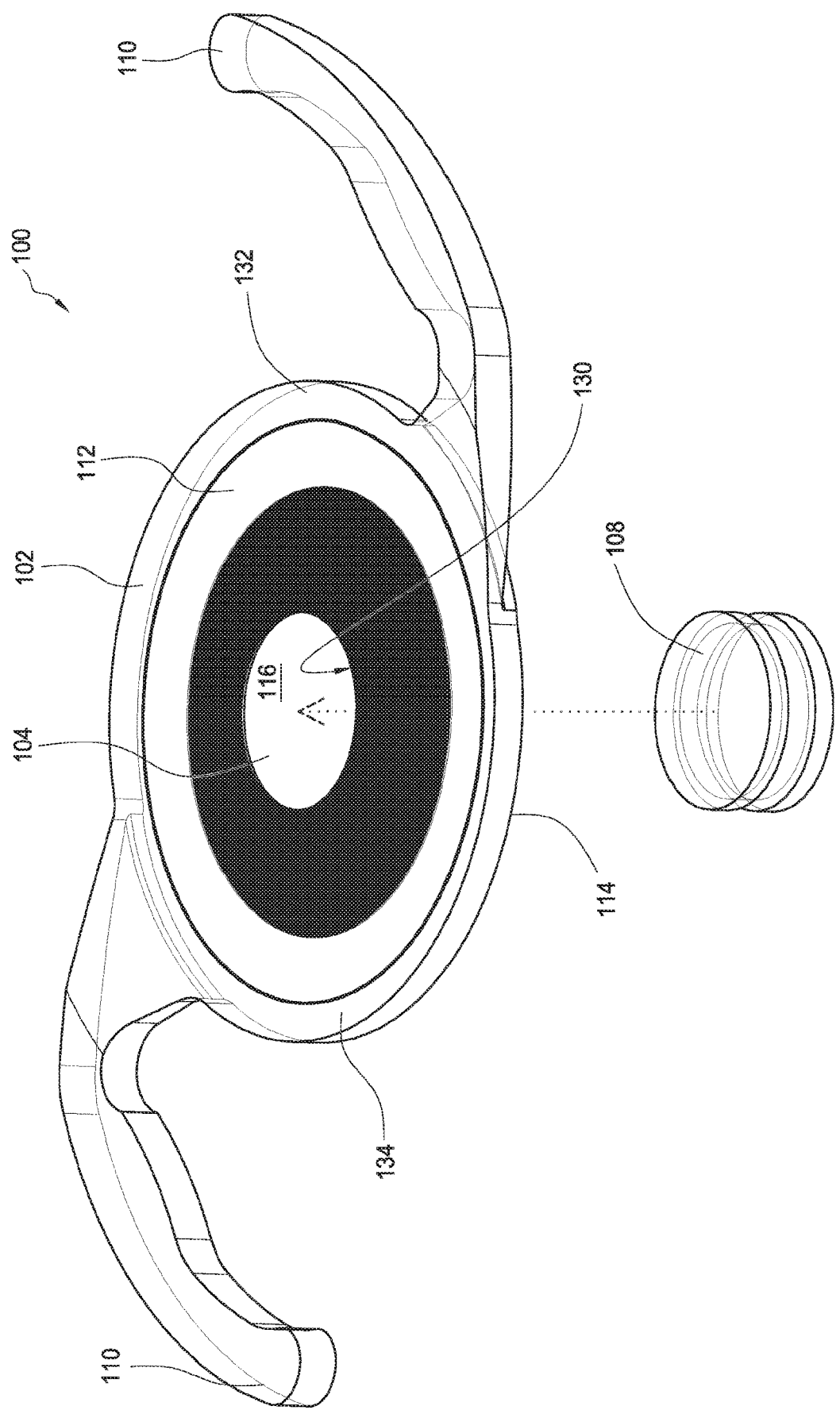

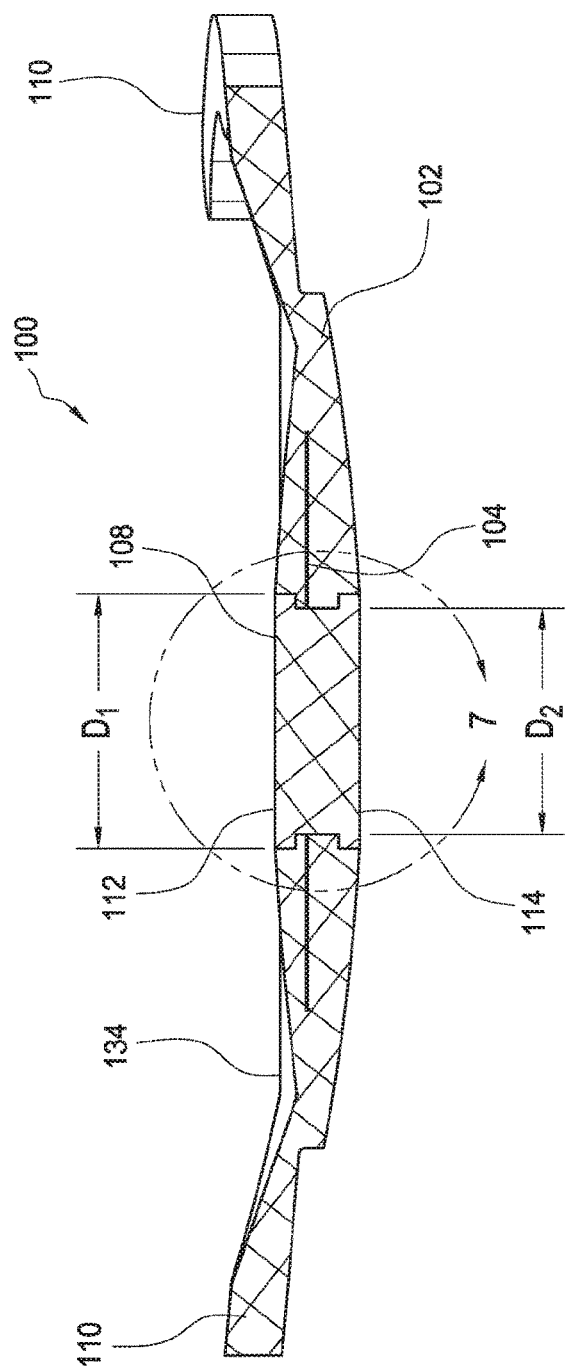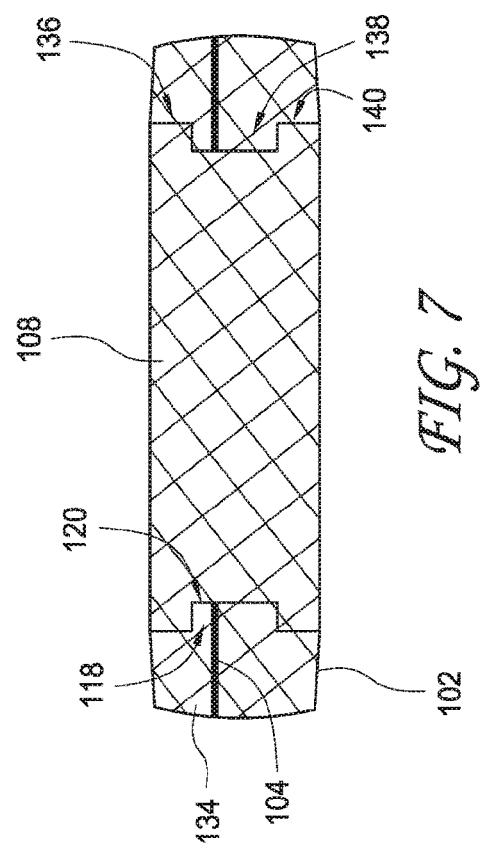

INTRAOCULAR IMPLANT WITH REMOVABLE OPTIC

BACKGROUND

Field

This application relates generally to the field of intraocular devices.

Description of the Related Art

The human eye functions to provide vision by transmitting and focusing light through a clear outer portion called the cornea, and further refining the focus of the image onto a retina by way of a crystalline lens. The quality of the focused image depends on many factors including the size and shape of the eye, and the transparency of the cornea and the lens.

The optical power of the eye is determined by the optical power of the cornea and the crystalline lens. In a normal, healthy eye, sharp images of distant objects are formed on the retina (emmetropia). In many eyes, images of distant objects are either formed in front of the retina because the eye is abnormally long or the cornea is abnormally steep (myopia), or formed in back of the retina because the eye is abnormally short or the cornea is abnormally flat (hyperopia).

Some people suffer from cataracts in which the crystalline lens undergoes a loss of transparency. In such cases, the crystalline lens can be removed and replaced with an intraocular lens (IOL). However, some intraocular lenses may leave defects in a patient's non-distance eyesight.

SUMMARY

Intraocular lenses are often uniquely molded and then machined to include the appropriate optical properties. However, if the intraocular lens is not perfectly milled across the entire anterior and posterior surfaces of the intraocular lens, the intraocular lens can have the incorrect power and become unusable. To remove this manufacturing complexity, an intraocular lens, or implant, can be formed where only a central region of the intraocular implant has optical power. This powered portion of the implant (also referred to herein as a lens or optic) can interface or mechanically couple with a lens holder having negligible (e.g., less than 0.25 diopters) or no optical power. In this configuration, the same lens holder can interface with different powered lenses. Because the lens holder has negligible or no power, the anterior and posterior surfaces of the lens holder do not need to be perfectly milled to specification. This reduces the number of unique steps needed to create an intraocular lens and, in particular, an IOL with a small aperture to increase depth of focus.

As an example, the intraocular implant can include a lens holder and an optic. The lens holder can include an outer periphery and an inner periphery. The inner periphery of the lens holder can define an aperture extending from an anterior surface of the lens holder to a posterior surface of the lens holder. At least a portion of the lens holder can be substantially opaque to visible light. The substantially opaque portion can be disposed about the aperture. An optic can be positioned in the aperture and mechanically coupled or interlocked with the inner periphery of the lens holder. The aperture may be configured to increase depth of focus in a human patient when the intraocular implant is implanted in an eye of the human patient.

As another example, the intraocular implant can include a lens holder and a powered optic. The lens holder can include an outer periphery and an inner periphery. The inner periphery of the lens holder can define an aperture extending from an anterior surface of the lens holder to a posterior surface of the lens holder. The lens holder can have negligible or no power, or can be powered. The powered optic can be positioned in the aperture and mechanically coupled or interlocked with the lens holder. The aperture may be configured to increase depth of focus in a human patient when the intraocular implant is implanted in an eye of the human patient.

A method of manufacturing the intraocular implant can include forming a lens holder. The lens holder can include an outer periphery and an inner periphery. The inner periphery of the lens holder can include an aperture extending from an anterior surface of the lens holder to a posterior surface of the lens holder. The method can also include forming an optic. After forming the lens holder and the optic, the method can include inserting the optic into the aperture and mechanically coupling or interlocking the optic with the inner periphery of the lens holder.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No aspects of this disclosure are essential or indispensable.

BRIEF DESCRIPTION OF THE DRAWINGS

Various embodiments are depicted in the accompanying drawings for illustrative purposes and should in no way be interpreted as limiting the scope of the embodiments. Furthermore, various features of different disclosed embodiments can be combined to form additional embodiments, which are part of this disclosure.

FIG. 2 illustrates a partial exploded view of the intraocular implant shown in FIG. 1.

FIG. 6 illustrates a cross-section of the intraocular implant taken across line 6-6 in FIG. 4.

FIG. 7 illustrates an enlarged partial view taken along section line 7 in FIG. 6.

DETAILED DESCRIPTION

Figure 1:
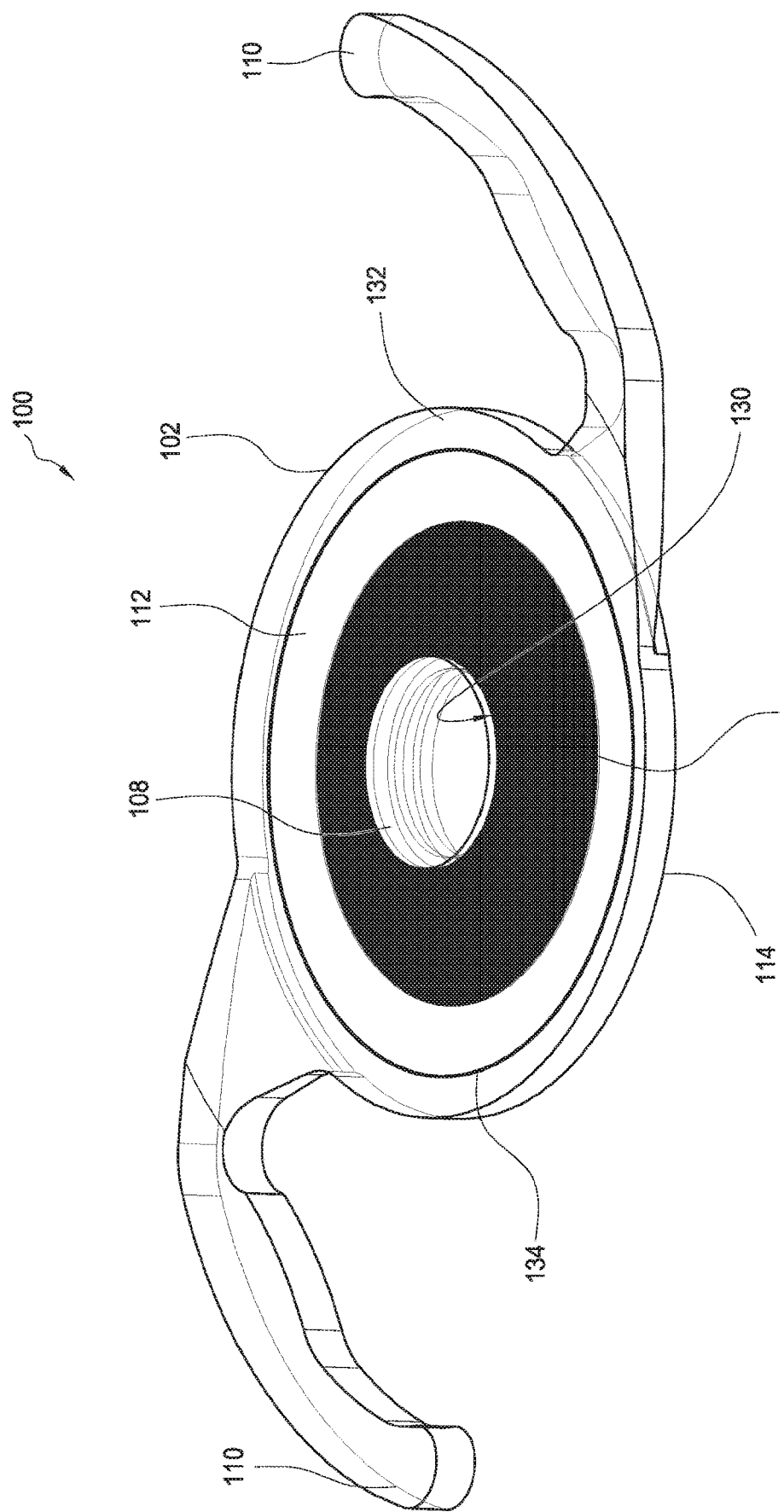
FIG. 1 illustrates a perspective view of an intraocular implant including an optic mechanically coupled with a lens holder.
Figure 4:
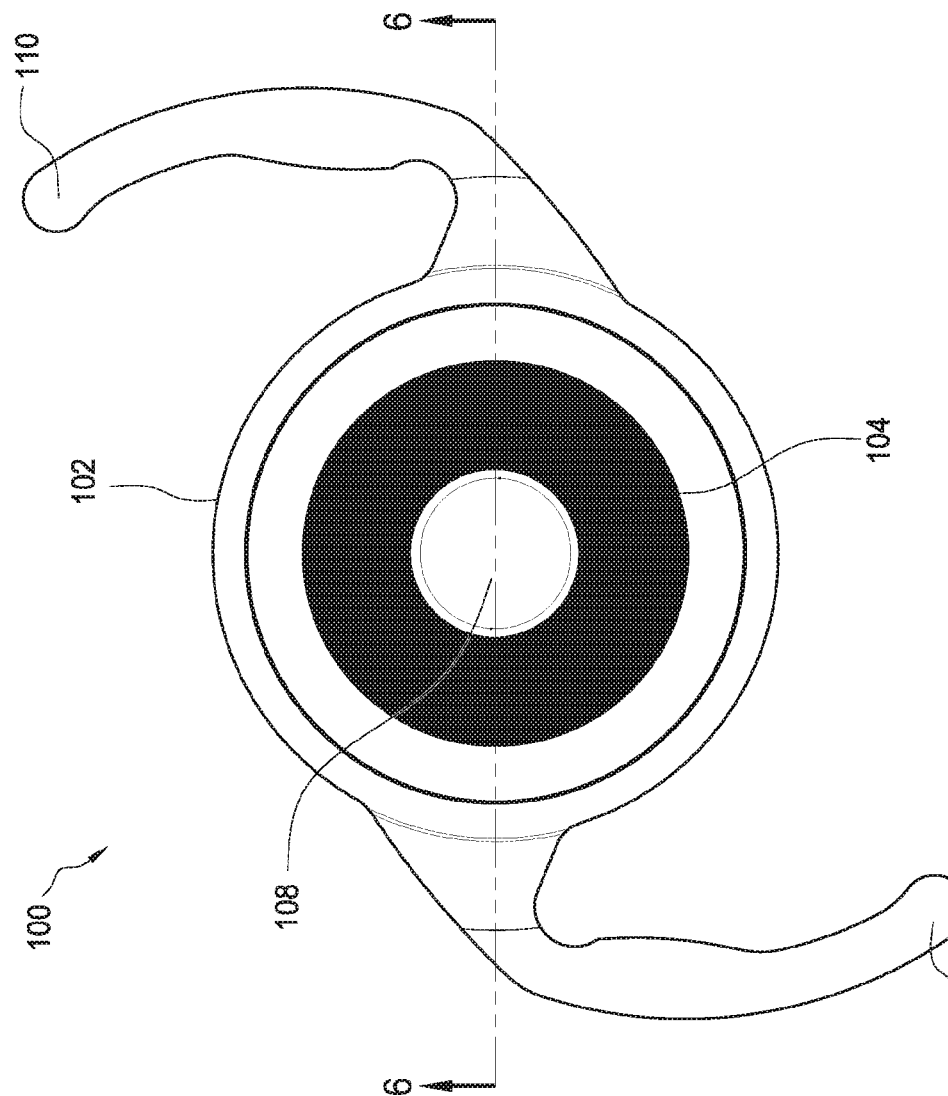
FIG. 4 illustrates a top view of the intraocular implant shown in FIG. 1.
Figure 3:
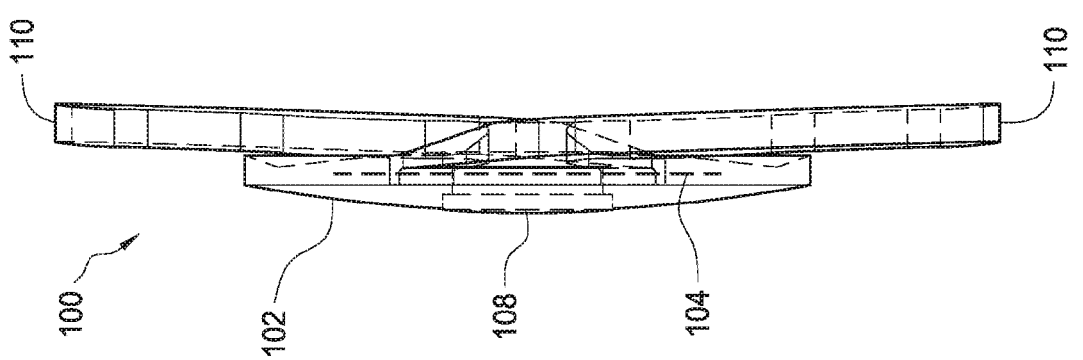
FIG. 3 illustrates a side view of the intraocular implant shown in FIG. 1.

Patients who undergo intraocular lens (IOL) implantation surgery may still suffer from defects in their non-distance eyesight. One technique for treating such defects is by including a small aperture within the IOL that allows light to pass through to the retina to increase depth of focus. The light rays that pass through the mask within the IOL converge at a single focal point on the retina, while the light rays that would not converge at the single point on retina are blocked by the mask. This disclosure describes methods for manufacturing an implant, such as an IOL, having an aperture. The intraocular implant may be implanted in the anterior chamber or the posterior chamber of the eye. In the posterior chamber, the implant may be fixated in the ciliary sulcus, in the capsular bag, or anywhere an intraocular implant is fixated.

FIGS. 1-7 illustrate an intraocular implant 100 having a lens holder 102 and an optic 108. As shown in FIG. 2, the lens holder 102 and the optic 108 are separate components that can be coupled together to form the intraocular implant 100 shown in FIG. 1. The optic 108 can be inserted through an aperture 116 of the lens holder 102 such that an interfacing structure of the optic 108 mechanically couples or interlocks with a corresponding interfacing structure of the lens holder 102.

As shown in FIG. 2, the lens holder 102 includes a main body 134 having an inner periphery 130 and an outer periphery 132. The main body 134 can be generally circular with an outer diameter between about 5 mm and about 10 mm, for example about 6 mm. The inner periphery 130 of the main body 134 defines the aperture 116 through which the optic 108 is inserted. At any axial position of the aperture 116, the aperture 116 can have a diameter of at least about 0.85 mm and/or less than or equal to about 2.2 mm, at least about 1.1 mm and/or less than or equal to about 2.0 mm, or at least about 1.4 mm and/or less than or equal to about 1.8 mm.

The lens holder 102 can have an anterior surface 112 and a posterior surface 114. Each of the anterior and posterior surfaces 112, 114 can be curved or planar. For example, as shown FIG. 6, the lens holder 102 can be biconvex. The lens holder 102 can have negligible or no optical power. Because the lens holder 102 has negligible or no optical power, manufacture of the IOL 100 is simplified compared to an IOL in which the entire main body 134 is optically powered.

Although some of the embodiments described herein are discussed with respect to a lens holder 102 having negligible or no optical power, in other configurations, the lens holder 102 may have optical power, for example the same or different optical power as the optic 108.

The intraocular implant 100 can include haptics 110 for positioning the intraocular implant 100 in the eye. The haptics 110 can be separately attached to the lens holder 102 or integrally formed with and include a same material as the main body 134. The main body 134 and haptics 110 can take on any of the configurations described in U.S. Pat. No. 9,492,272, which is hereby incorporated by reference in its entirety herein.

The aperture 116 can extend from the anterior surface 112 of the main body 134 to the posterior surface 114 of the main body 134. A diameter of the aperture 116 at the anterior surface 112 and/or the posterior surface 114 can be greater than a diameter of the aperture 116 taken at a transverse midline of the aperture 116. As shown in FIGS. 6 and 7, the aperture 116 can have an anterior region 136, a central region 138, and a posterior region 140. A diameter $D_2$ of the central region 138 can be less than a diameter $D_1$ of the anterior region 136 and/or the posterior region 140 (see FIG. 6). The lens holder 102 can include a projection 118 that defines the reduced diameter section of the aperture 116. The projection 118 can be an annular projecting rib in a central region 138 of the aperture 116. When viewed in cross-section, the projection 118 can form a stepped profile. For example, the projection 118 can include an anterior ledge, a posterior ledge, and a sidewall therebetween. As described in further detail below, the projection 118 can mechanically couple or mechanically interlock with the optic 108.

Alternatively, a diameter of the central region can be greater than a diameter of the anterior region and/or the posterior region of the aperture. The lens holder can include a recess that defines the increased diameter section of the aperture. The recess can be an annular recess in a central region of the aperture that receives a projection on the optic.

The lens holder 102 can include one or more materials. For example, the lens holder material can include a hydrophobic material and/or a low-viscosity material. The lens holder material can include polymers (e.g. PMMA, PVDF, polypropylene, polycarbonate, PEEK, polyethylene, acrylic, acrylic copolymers, polystyrene, PVC, polysulfone, silicone) or hydrogels. The main body 134 of the lens holder 102 can be substantially transparent to visible light. In some embodiments, the main body 134 of the lens holder 102 can be substantially opaque to visible light and substantially transparent to near infrared (IR) light. Further near-IR details are disclosed in U.S. Pat. No. 9,545,303, which is hereby incorporated by reference in its entirety herein.

The lens holder material can include an ultraviolet light absorber to protect the eye from ultraviolet light. The lens holder material can also include a light-sensitive initiator to allow the lens holder material to be photo-cured by exposure to light. The light-sensitive initiator can include various biocompatible initiators, including, but not limited to, acylphosphine oxide initiators, such as Irgacure® 819.

At least a portion of the main body 134 adjacent to and surrounding the aperture 116 can include opacity to prevent substantially all or all visible light from being transmitted through the portion of the main body 134. For example, the portion having opacity can prevent transmission of at least about 92 percent, at least about 95 percent, or at least about 99 percent of all incident, visible light.

At least a partial or entire thickness of the main body 134 can include the opacity. For example, the lens holder 102 can include a mask 104 that is substantially or completely opaque to visible light. The mask 104 can be positioned on a posterior or anterior surface of the main body 134 or embedded within the main body 134. For example, the mask 104 can be centrally embedded in the main body 134. As shown in FIGS. 6 and 7, the mask 104 can be positioned around the central region 138 of the aperture 116. An inner periphery of the mask 104 abuts or forms a part of the inner periphery 130 of the main body 134. The mask 104 can take on any of the configurations or positions described in U.S. Pat. No. 9,492,272, which is hereby incorporated by reference in its entirety herein. The mask 104 may also be formed using any of the methods described in U.S. Publication No. 2019/0076235, which is hereby incorporated by reference in its entirety herein.

The mask 104 can be symmetrical about a central axis. For example the mask 104 can be circular. The mask 104 can have an outer diameter of at least about 3 mm and/or less than about 6 mm, such as at least about 3 mm and/or less than or equal to about 4 mm, for example about 3.2 mm. An inner diameter of the mask 104 can be any size that is effective to increase the depth of focus of an eye of a patient. The mask 104 can include an aperture with a diameter of at least about 0.85 mm and/or less than or equal to about 2.2 mm, at least about 1.1 mm and/or less than or equal to about 2.0 mm, or at least about 1.4 mm and/or less than or equal to about 1.8 mm. In other configurations, the inner diameter of the mask 104 may be sized for any suitable optic.

A thickness of the mask 104 can be within a range from greater than zero to about 0.6 mm, about 1 micron to about 40 microns, about 5 microns to about 20 microns, about 5 microns to about 15 microns, or otherwise. For example, the thickness of the mask 104 can be about 15 microns, about 10 microns, about 8 microns, about 5 microns, or otherwise.

The mask material can be naturally opaque or treated with a dye or other pigmentation agent to render the mask 104 substantially or completely opaque. The mask material can be the same material or a different material than the lens holder material. For example, the mask material can include a polymeric material (e.g. PMMA, PVDF, polypropylene, polycarbonate, PEEK, polyethylene, acrylic, acrylic copolymers, polystyrene, PVC, polysulfone), hydrogels, or fibrous materials.

As another example, the mask can include a photochromic material. When implanted, the photochromic material can temporarily or permanently darken to enhance near vision. Further photochromic material details are disclosed in U.S. Pat. Nos. 9,204,962 and 9,545,303, which are hereby incorporated by reference in their entireties herein.

As another example, the mask can block the transmission of substantially all visible light while remaining transparent to the near IR light used in ocular imaging. The mask can permit the transmission of electromagnetic radiation with a wavelength between about 750 nm and about 1500 nm through mask 104. The mask 104 can be dyed or otherwise treated to provide these transmissivity properties. Further near-IR details are disclosed in U.S. Pat. No. 9,545,303, which is hereby incorporated by reference in its entirety herein.

The mask 104 can be molded, printed, formed, etched, laser-created, heat- or light-created, or otherwise created in or attached to the main body 134. For example, the main body 134 can be cast molded around the mask 104. During the molding process, the mask 104 can be centered on a protruding pin in the mold. When the main body 134 is removed from the mold, the protruding pin leaves behind a void that is the aperture 116. The mold can be shaped to form an interfacing structure in the inner periphery 130 of the lens holder 102, or after molding, the lens holder 102 can be machined to form the interfacing structure in the inner periphery 130 of the lens holder 102. Formation of the lens holder 102 and centration of the mask 104 can also be performed using any of the techniques described in U.S. Pat. Nos. 9,492,272 and 9,427,922, which are hereby incorporated by reference in their entireties herein.

Figure 5C:
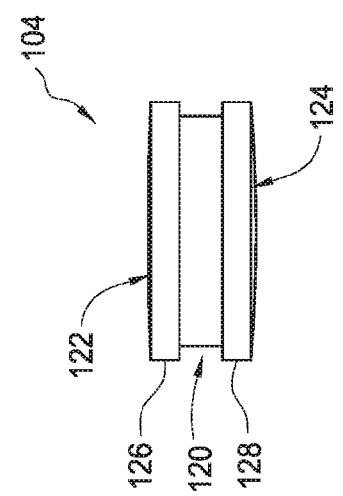
FIGS. 5A-5C illustrate various views of the optic shown in FIG. 2.
Figure 5B:
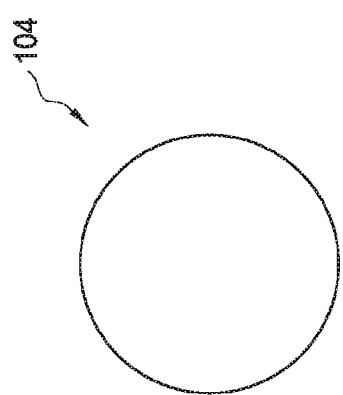
Figure 5A:
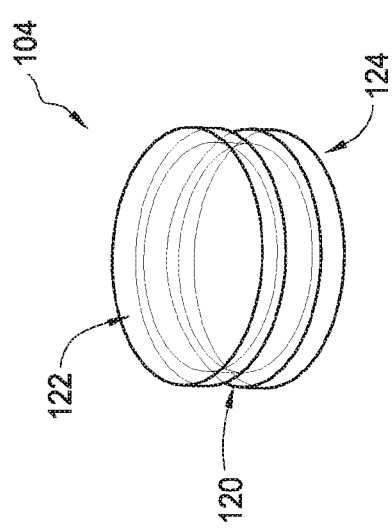
Figure 8:
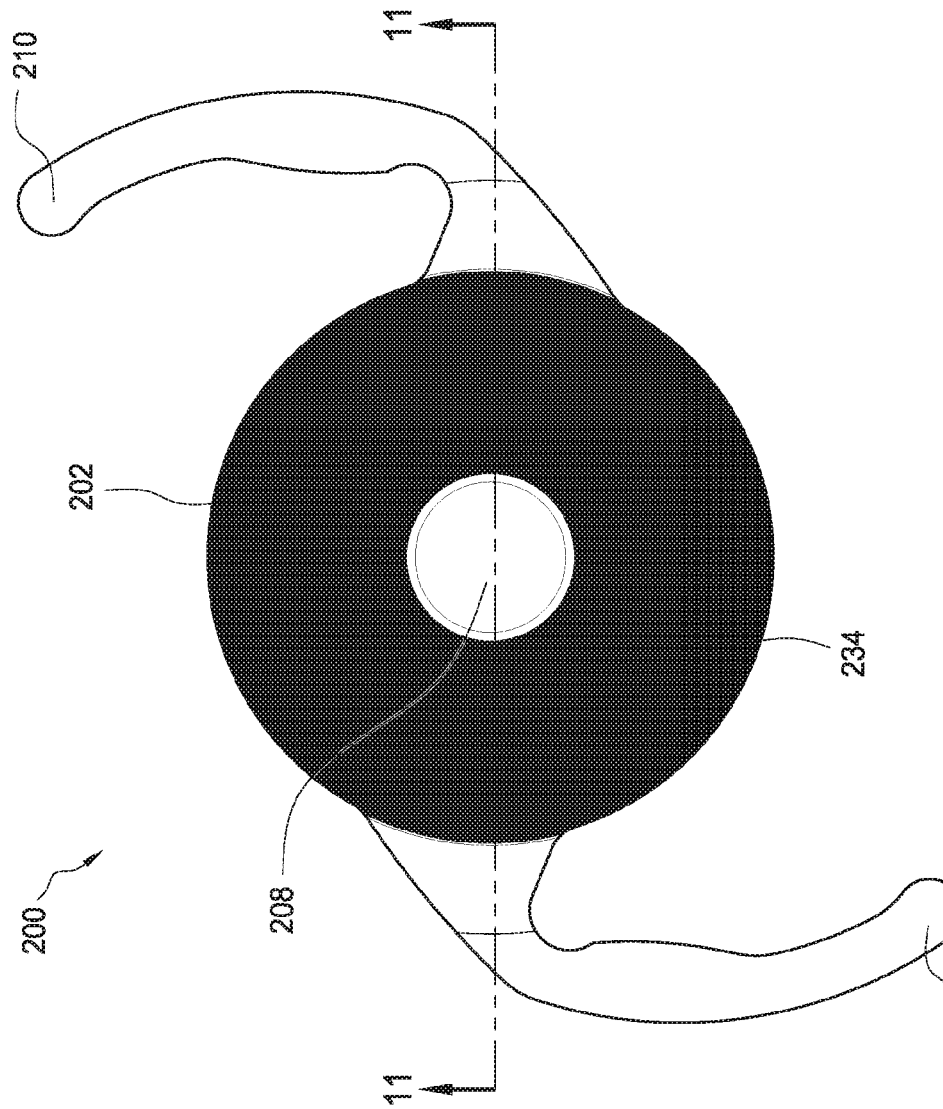
FIG. 8 illustrates a top view of another intraocular implant including an optic mechanically coupled with a lens holder.
Figure 9:
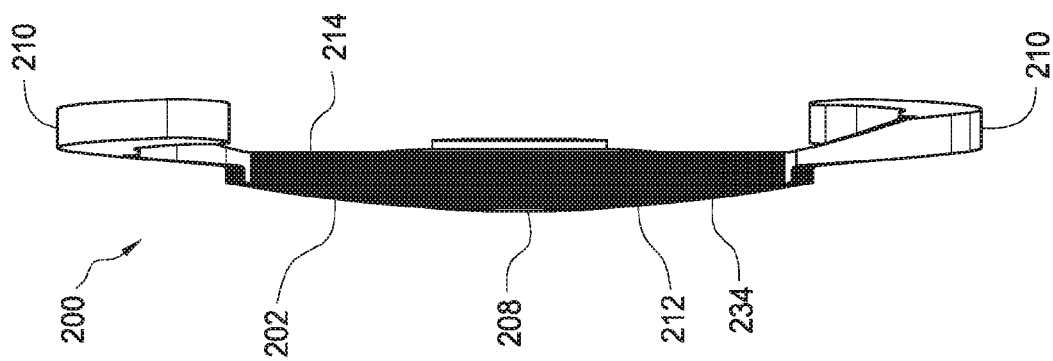
FIG. 9 illustrates a side view of the intraocular implant shown in FIG. 8.
Figure 10A:
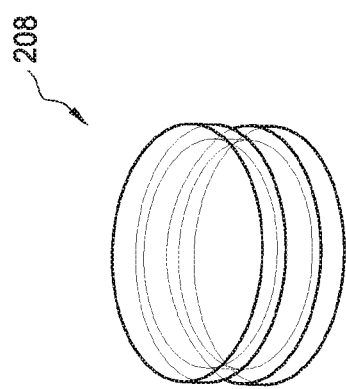
FIGS. 10A-10C illustrate various view of the optic shown in FIG. 8.
Figure 10B:
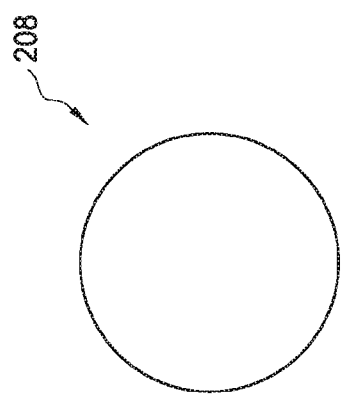
Figure 10C:
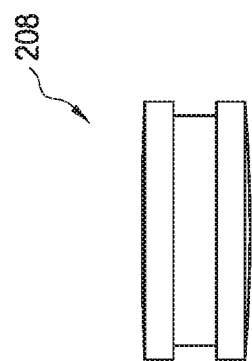
Figure 11:
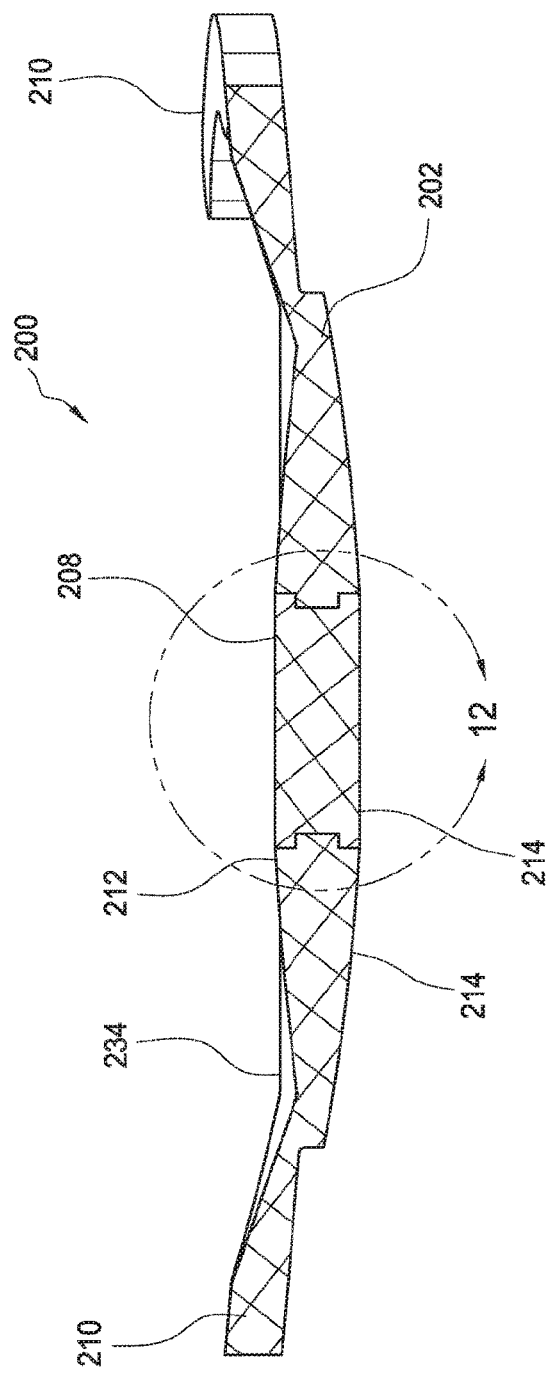
FIG. 11 illustrates a cross-section of the intraocular implant taken across line 11-11 in FIG. 8.
Figure 12:
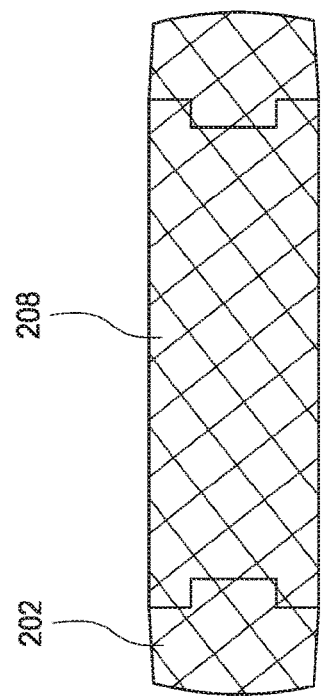
FIG. 12 illustrates an enlarged partial view taken along section line 12 in FIG. 11.

FIGS. 5A-5C illustrate different views of a powered optic 108. Because the lens holder 102 may have negligible or no optical power, different powered optics 108 can be used with the same lens holder 102. For example, a kit could be provided with different powered optics 108 and a single lens holder 102. As another example, a kit could be provided with different powered optics 108 and different-sized lens holders 102. Each of the powered optics 108 can be shaped to interface with any one of the different-sized lens holders 102.

The optic 108 can include an anterior region 122, a central region 120, and a posterior region 124. A diameter of the anterior region 122 and the posterior region 124 can be greater than a diameter of the central region 120. For example, the central region 120 can include an annular recess configured to interface with and mechanically interlock with the protrusion 118 on the inner periphery 130 of the lens holder 102. A thickness of the central region 120 can be the same or different than a thickness of the anterior region 122 and/or the posterior region 124. For example, the thickness of the central region 120 can be greater than the thickness of the anterior region 122 and the posterior region 124. Alternatively, the outer profile of the optic 108 can be inverted such that a diameter of the central region 120 is greater than a diameter of the anterior region 122 and the posterior region 124.

As shown in FIG. 5C, the optic 108 can be biconvex. The anterior and posterior surfaces 108 can include the same or different curvatures. The lens holder 102 can be shaped such that curvatures of the anterior surface 112 and the exterior surface 114 of the main body 134 are continuous with the curvatures of the anterior and posterior surfaces of the optic 108. When the optic 108 is inserted into the lens holder 102, the anterior and posterior surfaces of the optic 108 can be flush with the anterior and posterior surfaces of the main body 134 (see FIG. 6). The anterior and posterior surfaces of the intraocular implant 100 can include a continuous profile, such as a continuous curvature without any steps or breaks. A side wall 126 of the anterior region 122 and/or a side wall 128 of the posterior region 124 can be vertical, beveled, stepped, or otherwise shaped.

The optic 108 can include a same or different material than the main body 134 and/or the mask 134. The optic material can include a hydrophobic material and/or a low-viscosity material. The optic material can include polymers (e.g. PMMA, PVDF, polypropylene, polycarbonate, PEEK, polyethylene, acrylic, acrylic copolymers, polystyrene, PVC, polysulfone, silicone) or hydrogels.

The optic 108 and/or the lens holder 102 may include indicia, for example on an anterior surface thereof, to assist in placement of the optic 108 in the lens holder 102 and/or in the eye. For example, the indicia can be configured to align the optic 108 with particular ocular anatomy.

The main body 134 can be more flexible than the optic 108 to facilitate insertion of the optic 108 into the main body 134. In this configuration, the aperture 116 flexes to permit insertion of the optic 108. As an example, the main body 108 can include PMMA and the main body 134 can include hydrophobic acrylic.

As described above, the optic 108 is coupled to the lens holder 102. Rather than being integrally molded or formed, the optic 108 can be separately formed and mechanically coupled the lens holder 102. For example, the optic 108 and the lens holder 102 can be mechanically interlocked by a press-fit, snap-fit, threaded interface, or otherwise.

As shown in FIGS. 6 and 7, the recess in the central region 120 of the optic 108 can interface and mechanically interlock with the protrusion 118 in the central region 138 of the aperture 116. The recess can be an annular recess in the central region 120 of the optic 108 (see FIGS. 5A-5C). The protrusion 118 can be an annular rib in the central region 118 of the aperture 116. When the optic 108 is inserted into the aperture 116, the optic 108 and/or the aperture 116 can undergo some deflection and recover to its original mechanical and optical state when properly assembled.

Alternatively, the optic 108 can include an annular rib projecting from a central region of the optic 108, and the lens holder 102 can include a recess in a central region of the inner periphery 130 of the lens holder 102. Although FIGS. 6 and 7 illustrate the optic 108 including one recess and the main body 134 including one protrusion 118, the interfacing structures of the intraocular implant 100 could include multiple, longitudinally spaced apart recesses and protrusions. Further, the recess and protrusion could be shaped differently than shown in the figures. For example, the recess and the protrusion could include corresponding v-shaped profiles, such that anterior and posterior edges of each of the recess and the protrusion meet at an apex.

When coupled together, the anterior region 136, central region 138, and posterior region 140 of the aperture 116 can receive the corresponding anterior region 122, central region 120, and posterior region 124 of the optic 108. A posterior edge of the anterior region 122 of the optic 108 can abut an anterior edge of the central region 138 of the aperture 116. An anterior edge of the posterior region 128 of the optic 108 can abut a posterior edge of the central region 138 of the aperture.

With reference to FIGS. 8-12, another example intraocular implant 200 is shown. The intraocular implant 200 resembles or is identical to the intraocular implant 100 discussed above in many respects. Accordingly, numerals used to identify features of the intraocular implant 100 are incremented by a factor of one hundred (100) to identify like features of the intraocular implant 200. This numbering convention generally applies to the remainder of the figures. Any component or step disclosed in any embodiment in this specification can be used in other embodiments.

Similar to the intraocular implant 100 shown in FIGS. 1-7, the intraocular implant 200 includes an optic 208 mechanically coupled or mechanically interlocked with a lens holder 202. These two components can mechanically couple or mechanically interlock in the same manner described above with respect to FIGS. 1-7. The optic 208 shown in FIGS. 10A-10C can include the similar or identical features to the optic 108 shown in FIGS. 5A-5C. However, unlike the lens holder 102, the lens holder 202 does not include a mask.

The entire main body 234, from an anterior surface 212 of the main body 234 to a posterior surface 214 of the main body 234, includes opacity to prevent substantially all or all visible light from being transmitted through the any portion of the main body 234. For example, the main body 234 can prevent transmission of at least about 92 percent, at least about 95 percent, or at least about 99 percent of all incident, visible light.

The entire main body 234 can be constructed from the same material(s). The main body material can be naturally opaque or treated with a dye or other pigmentation agent to render the main body 234 substantially or completely opaque. The main body material can include a polymeric material (e.g. PMMA, PVDF, polypropylene, polycarbonate, PEEK, polyethylene, acrylic, acrylic copolymers, polystyrene, PVC, polysulfone), hydrogels, or fibrous materials.

As another example, the main body material can include a photochromic material. When implanted, the photochromic material can temporarily or permanently darken to enhance near vision. Further photochromic material details are disclosed in U.S. Pat. Nos. 9,204,962 and 9,545,303, which are hereby incorporated by reference in their entireties herein.

As another example, the main body 234 can block the transmission of substantially all visible light while remaining transparent to the near IR light used in ocular imaging. For example, the main body 234 can permit the transmission of electromagnetic radiation with a wavelength between about 750 nm and about 1500 nm through mask 104. The main body 234 be dyed or otherwise treated to achieve these transmissivity properties. Further near IR details are disclosed in U.S. Pat. No. 9,545,303, which is hereby incorporated by reference in its entirety herein.

The intraocular implant 200 can include haptics 210 for positioning the intraocular implant 200 in the eye. The haptics 210 can be separately attached to the lens holder 202 or integrally formed with and include the same material(s) as the lens holder 202. For example, the haptics 210 can include the same opacity as the main body 234.

Terminology

Although certain intraocular implants have been described herein in connection with specific optics or lenses, the optic may be any suitable optic for an intraocular lens, including but not limited to, a spherical lens, a monofocal lens, a multifocal lens, an aspheric lens, a photochromic lens, or a toric lens.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

The terms "approximately," "about," and "substantially" as used herein represent an amount close to the stated amount that still performs a desired function or achieves a desired result. For example, unless otherwise defined herein, the terms "approximately," "about," and "substantially" may refer to an amount that is within less than 10% of the stated amount, as the context may dictate.

The ranges disclosed herein also encompass any and all overlap, sub-ranges, and combinations thereof. Language such as "up to," "at least," "greater than," "less than," "between" and the like includes the number recited. Numbers preceded by a term such as "about" or "approximately" include the recited numbers. For example, "about 3 mm" includes "3 mm."

Although certain embodiments and examples have been described herein, it will be understood by those skilled in the art that many aspects of the methods and IOLs shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

For purposes of this disclosure, certain aspects, advantages, and novel features are described herein. It is to be understood that not necessarily all such advantages may be achieved in accordance with any particular embodiment.

Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

What is claimed is:

1. An intraocular lens (IOL) comprising:
   a lens holder comprising an outer periphery and an inner periphery, the inner periphery defining an aperture, the aperture extending from an anterior surface of the lens holder to a posterior surface of the lens holder, an annular portion of the lens holder being substantially opaque to visible light, the substantially opaque annular portion being disposed about the aperture and embedded within the lens holder; and
   an optic positioned in the aperture and mechanically coupled with the inner periphery of the lens holder;
   wherein the aperture comprises a diameter of between about 0.85 mm to about 2.2 mm;
   wherein the aperture is sized and configured to increase depth of focus in a human patient when the intraocular lens is implanted in an eye of the human patient;
   wherein the optic includes an anterior region, a central region, and a posterior region, a diameter of the anterior region and a diameter of the posterior region are greater than a diameter of the central region of the optic;
   wherein the aperture includes an anterior region, a central region, and a posterior region, a diameter of the anterior region of the aperture and a diameter of the posterior region of the aperture are greater than a diameter of the central region of the aperture;
   wherein the central region of the optic is sized and configured to interface and mechanically interlock with the central region of the aperture.

2. The intraocular lens of claim 1, wherein the lens holder is powered.

3. The intraocular lens of claim 1, wherein the entire lens holder is substantially opaque to visible light.

4. The intraocular lens of claim 1, wherein the substantially opaque portion of the lens holder is substantially transparent to at least some non-visible electromagnetic radiation with a wavelength between 750 nm and about 1500 nm to facilitate examining ocular tissue posterior to the intraocular implant.

5. The intraocular lens of claim 1, wherein the optic comprises acrylic.

6. The intraocular lens of claim 1, wherein the lens holder comprises acrylic.

7. The intraocular lens of claim 1, wherein the lens holder comprises a first material and the optic comprises a second material, the second material being different from the first material.

8. The intraocular lens of claim 1, wherein the lens holder comprises haptics.

9. The intraocular lens of claim 1, wherein the lens holder is integrally formed as one piece.

* * * * *